United States Patent
Lara Magallanes et al.

(10) Patent No.: US 9,863,891 B1
(45) Date of Patent: Jan. 9, 2018

(54) VEHICLE FOR EXTERNAL INSPECTION OF PIPES

(71) Applicant: Corporación Mexicana de Investigación en Materiales, S.A. de C.V, Saltillo (Coahuila) (MX)

(72) Inventors: Juan Antonio Lara Magallanes, Saltillo (MX); Elmer Sanchez Rivero, Saltillo (MX); Jesús Héctor Gerardo García Ortíz, Saltillo (MX)

(73) Assignee: Corporación Mexicana de Investigación en Materiales, S.A. de C.V., Saltillo (Coahuila) (MX)

( * ) Notice: Subject to any disclaimer, the term of this patent is extended or adjusted under 35 U.S.C. 154(b) by 0 days.

(21) Appl. No.: 15/370,549

(22) Filed: Dec. 6, 2016

(30) Foreign Application Priority Data

Nov. 7, 2016 (MX) .................. MX/A/2016/014532

(51) Int. Cl.
| | |
|---|---|
| F16L 55/00 | (2006.01) |
| G01B 11/02 | (2006.01) |
| G01B 11/06 | (2006.01) |
| G01N 17/04 | (2006.01) |
| G01N 21/952 | (2006.01) |
| G01N 21/88 | (2006.01) |

(52) U.S. Cl.
CPC ....... *G01N 21/952* (2013.01); *G01N 21/8806* (2013.01); *F16L 55/00* (2013.01); *G01B 11/02* (2013.01); *G01B 11/06* (2013.01); *G01N 17/04* (2013.01)

(58) Field of Classification Search
None
See application file for complete search history.

(56) References Cited

U.S. PATENT DOCUMENTS

| | | | | |
|---|---|---|---|---|
| 5,698,854 | A * | 12/1997 | Gupta .................... | G01N 23/18 250/358.1 |
| 6,782,631 | B1 * | 8/2004 | Face, III .................. | G01C 7/04 33/501.02 |
| 7,059,945 | B2 * | 6/2006 | Skinner .................... | B24C 1/08 118/307 |
| 7,159,477 | B2 * | 1/2007 | Edwin ..................... | G01B 5/08 33/501.08 |
| 7,594,448 | B2 * | 9/2009 | Jacobson ............. | G05D 1/0891 73/865.8 |
| 8,759,780 | B2 * | 6/2014 | Dobbs .................... | G01B 15/02 250/360.1 |
| 9,389,150 | B2 * | 7/2016 | Kimpel, Jr. ........... | G01M 99/00 |
| 2002/0036108 | A1 * | 3/2002 | Jeswine ............. | B62D 49/0621 180/164 |
| 2015/0336625 | A1 * | 11/2015 | Beard, III .............. | B62D 61/10 180/22 |

* cited by examiner

*Primary Examiner* — Tri Ton
*Assistant Examiner* — Jarreas C Underwood
(74) *Attorney, Agent, or Firm* — Abelman, Frayne & Schwab

(57) ABSTRACT

A vehicle for external inspection of tubing conformed by a body with a magnetic traction arrangement in its lower part and at least one inspection device mounted on the body; In which the magnetic drive arrangement includes two front magnetic wheels, a rear magnetic wheel coupled to two servomotors, one for controlling longitudinal advancement and another rudder servomotor for controlling the spin or rotation of this third wheel, and wherein the magnetic drive arrangement Inspection consists of a laser sensor coupled to a linear actuator.

16 Claims, 10 Drawing Sheets

VEHICLE FOR EXTERNAL INSPECTION OF PIPES

CROSS-REFERENCE TO RELATED APPLICATIONS

This application claims the benefit of priority under 35 U.S.C. 119 to Mexican Patent Application No. MX/a/2016/014532, filed Nov. 7, 2016, which is hereby incorporated by reference.

TECHNICAL FIELD OF THE INVENTION

The present invention relates to a vehicle for external inspection of pipelines. More particularly, the invention concerns an apparatus for non-destructive piping external inspection devices, with ease of movement out of the pipeline and with a displacement control on each magnetic wheel.

BACKGROUND OF THE INVENTION

At present, in the aeronautical, nuclear and oil industry, the preservation of the mechanical integrity in its mobile and stationary installations is being considered as part of its operational and safety policies, through maintenance and inspection actions, which in its most are made with the components operating, without programmed shutdowns of the plant, especially in the case of inspection.

In the case of the petroleum industry, by means of non-destructive test inspection provides information on discontinuities and defects in static components, such as pressure vessels and pipelines in service, information necessary to determine the structural condition of said components and their remaining life time, which helps to prevent potential problems and to make relevant decisions for repairs or maintenance, actions necessary to preserve the structural integrity and thus the safety of the facilities. Particularly in the processing facilities in the marine oil platforms there is a large number of pipes, which require periodic inspection to evaluate their mechanical integrity and increase the reliability and safety of their functionality, with the particularity that they are installed inside plants at sea, in confined spaces at different levels, even "flown" away from the main structure of the platform, which makes it difficult to inspect, making it necessary to use at least structures of tubular scaffolds, hanging scaffolds and ladders in order to be in direct contact with the pipe, however, the handling and safe installation of these scaffolds is a process that requires a significant investment of additional time to the inspection activities of considerably large extensions of pipelines, this logistical process includes the handling of this tool In the facilities of the plant, as well as its installation in each point where inaccessible pipe is found, turns out to be in many cases a limitation for the complete inspection of the plant.

In order to provide a solution to the aforementioned limitations, Antonio Ramirez Martinez, in patent application publication MXPA04012770, describes equipment which is capable of adhering to and moving through the ferromagnetic structures, either horizontally or vertically, with The purpose of measuring the wall thicknesses of said metal structures in an autonomous and robotic manner, or remotely controlled, using ultrasound as a means of measuring the thickness; The inspection equipment is constituted by a) a system of adherence; B) a traction system; C) a suspension system; D) a positioning system of the transducer of ultrasonic; E) a control system; (F) a remote control system; G) a data recording system; H) a verticality tracking system; And i) software.

Also Hayata Takashi and Nakahara Hirotaka describe in patent publication JP8338831, a surface inspection device, which is light and small to be stably executed even on a curved surface, constituted by at least one pair of magnetic wheels which are attracted towards the wall surface, are provided by vehicle on the right and left side thereof; An engine and a reduction mechanism that moves the wheels that are supported to the body with suspension mechanisms; A test ultrasonic, which is attached to the central section of the body via a spring. When the same rotation is applied to all the wheels, the body moves in a circumferential direction in a pipe and when different rotations are applied to the wheels $10a$, $10b$ and to the wheels $10c$, $10d$ respectively, the body is controlled for moved in spiral over the pipe.

While the curvature of the face varies, the controlled of each of the wheels $10a$-$10d$, of each of the motors and of each reduction mechanism may correspond to the variation of the curvature thus until reaching stability.

Xinjun Wu, Jianming Yuan, Chen Huang, Baijiang An and Yihua Kang in the Chinese patent CN101138994, describe a trailing robot for pipes with magnetic wheels for a vehicle, which includes four wheels, a permanent magnetic absorption mechanism and a mechanism of direction. The vehicle is made up of four wheels, which are installed in the frame of the vehicle. The set of wheels include a wheel frame, a wheel, a wheel handle, a handle steering, a speed reducer and an engine.

The mechanism of permanent magnetic absorption includes a small jaw and two magnets with inverted polarity. The steering mechanism includes a bracket, a chain drive wheel, a chain wheel drive shaft, a chain, a speed reducer and the engine. The permanent magnetic absorption mechanism is connected to the underside of the vehicle frame. The steering mechanism is fixed to the frame of the vehicle. The robot of the this document can trace on the outer surface of the pipe in an oblique pipe agreed on any route and can reach any external position of the pipe surface according to the requirements.

Also known from the state of the art is the document MX2010007204 (Magallanes), which discloses an apparatus for external inspection of pipes formed by a magnetic traction arrangement in its lower part and at least one inspection device mounted on the body, Magnetic drive comprises two magnetic wheels formed by a circular magnet, a toothed cap on its circumference disposed adjacent the magnet and a cap with at least a pair of notches on its circumference positioned on the opposite face of the magnet, this apparatus includes a Ultrasonic thickness measurement device, a video camera, a servomotor coupled to each wheel, these servo motors controlled by a software.

The solutions described by the patent documents offer an inspection vehicle for pipes with magnetic wheels of certain adhesion characteristics that allow it to adapt to the curvature of the surface for different situations, however, the metallic character with a smooth surface of the Wheels causes the coefficient of friction with respect to the surface to be inspected also metallic on the one to be displaced is minimal, also generate problems of displacement of the vehicle concretely when this one is with weldings or any other type of irregularities that usually exist in the walls of the pipeline or of the element on which the vehicle is to move, losing adhesion and preventing its movement, also none of the vehicles of the state of the art provides a complete control and stability in the advancement of the wheels allowing not only the advance front and back but also a controlled rotation.

In view of the foregoing, it is therefore necessary to provide a compact, lightweight, small-sized external pipe inspection apparatus which allows for the external inspection of complex arrangement pipes, with corrosion obstacles, welds or any other irregularities and Of small thicknesses of 101.6 mm in diameter (4 inches in diameter), where the magnetic wheels have a better adhesion for pipes of this type and that allow their translational and rotational displacement through these irregularities, conserving the force of adhesion and power Thus passing these obstacles. As well as performing the function of transporting external inspection devices such as video cameras, ultrasonic, laser sensors, etc. The present invention can be widely used for the maintenance, cleaning, and inspection work of the storage tanks.

SUMMARY OF THE INVENTION

In view of the foregoing and for the purpose of solving the constraints encountered, it is the object of the present invention to provide an apparatus for external inspection of pipes formed by a body with a magnetic traction arrangement in its lower part and at least one device of inspection mounted in the body; in which the magnetic tension arrangement includes three magnetic wheels, two front and one rear formed by: a magnet in a circular shape; a toothed cap on its circumference positioned adjacent one of the faces of said magnet; and a cap with at least one pair of holes in its flat face placed on the opposite side of the neodymium tablets; such that each pair of magnetic wheels are arranged in reverse configuration, the toothed lid of each magnetic wheel being oppositely disposed, and further the traction arrangement includes at least one magnet located in front of the magnetic wheels, so that each front wheel is coupled to a servomotor and the rear or rear wheel is coupled to a rudder servomotor and to an intelligent servomotor to give translational and rotational movement to the rear wheel.

BRIEF DESCRIPTION OF THE FIGURES

The characteristic details of the invention are described in the following paragraphs in conjunction with the accompanying figures, which are for the purpose of defining the invention but without limiting the scope thereof.

DETAILED DESCRIPTION OF THE INVENTION

Figure 1:
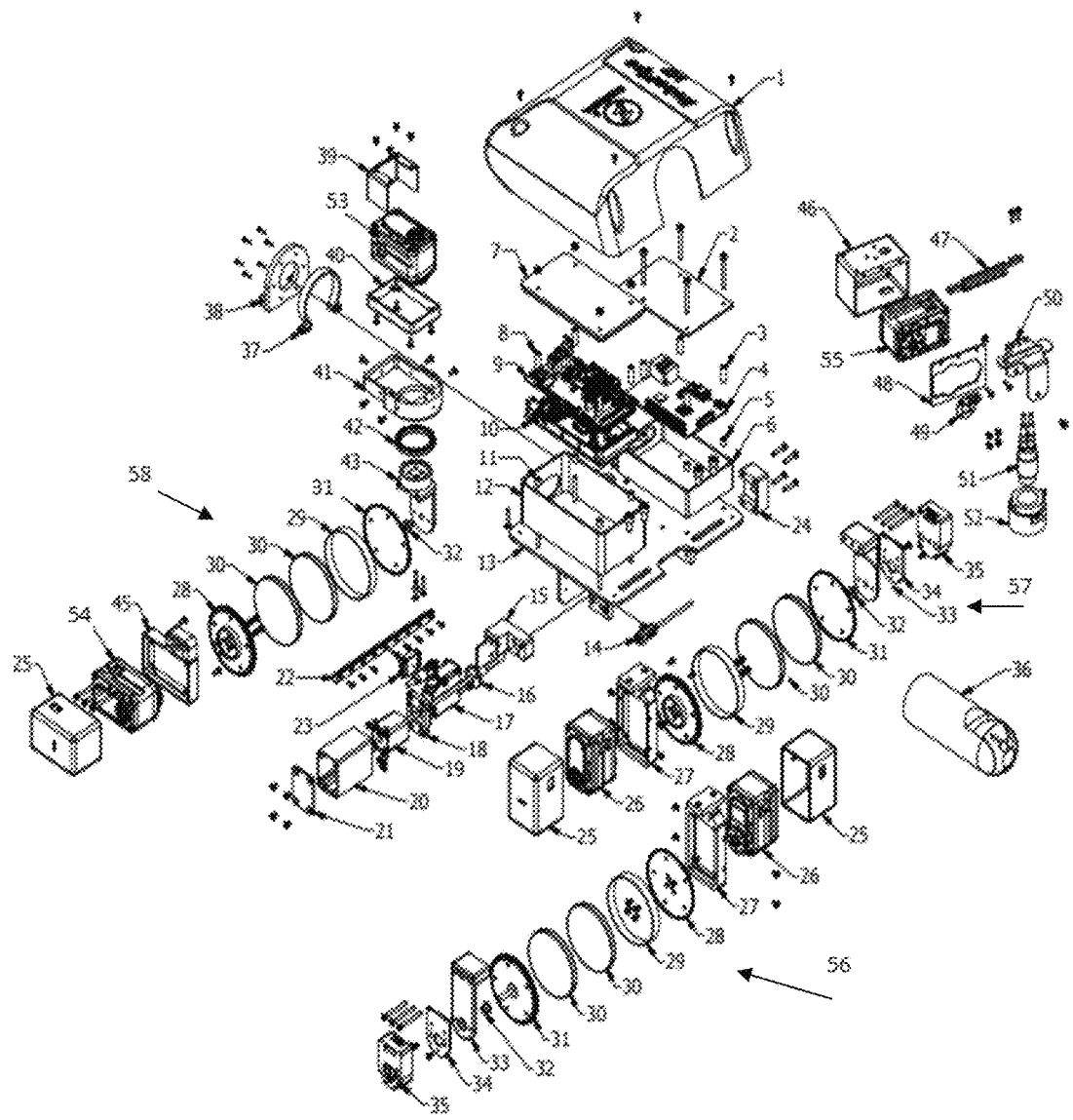
FIG. 1 shows an exploded isometric view of the vehicle for external inspection of pipes according to the invention.
Figure 2:
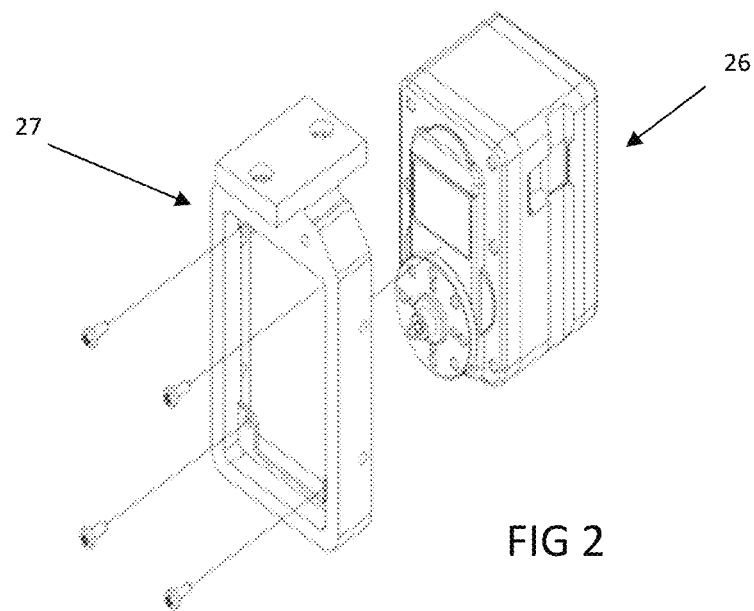
FIG. 2 illustrates an isometric view of the intelligent servomotor assembly with the servomotor support.
Figure 3:
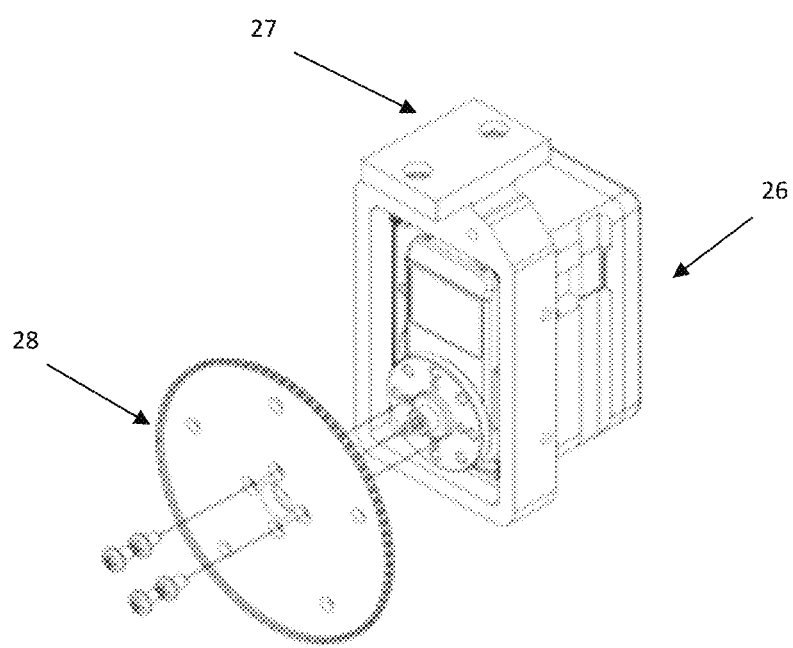
FIG. 3 illustrates an isometric view of the intelligent servomotor assembly with a first cover of wheel.
Figure 4:
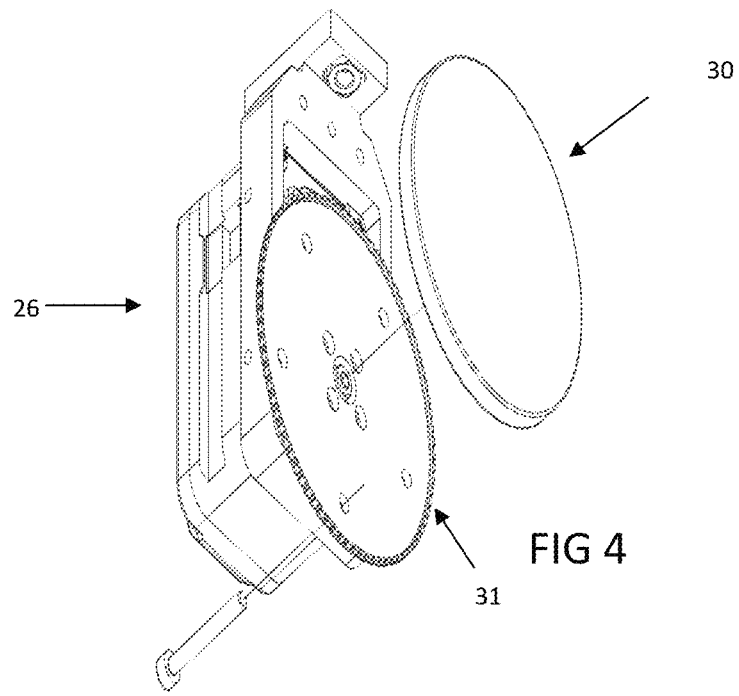
FIG. 4 illustrates an isometric view of the assembly of the first cover of wheel with the neodymium disc.
Figure 5:
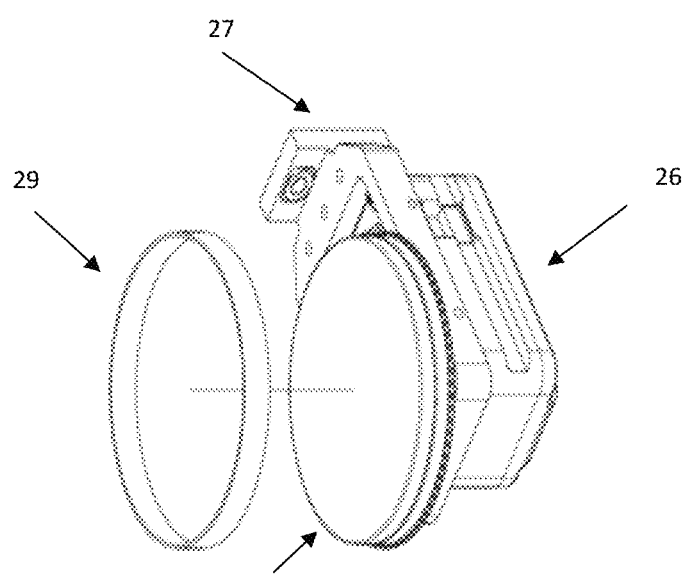
FIG. 5 illustrates an isometric view of the neodymium disco cover with the circular discs neodymium.
Figure 6:
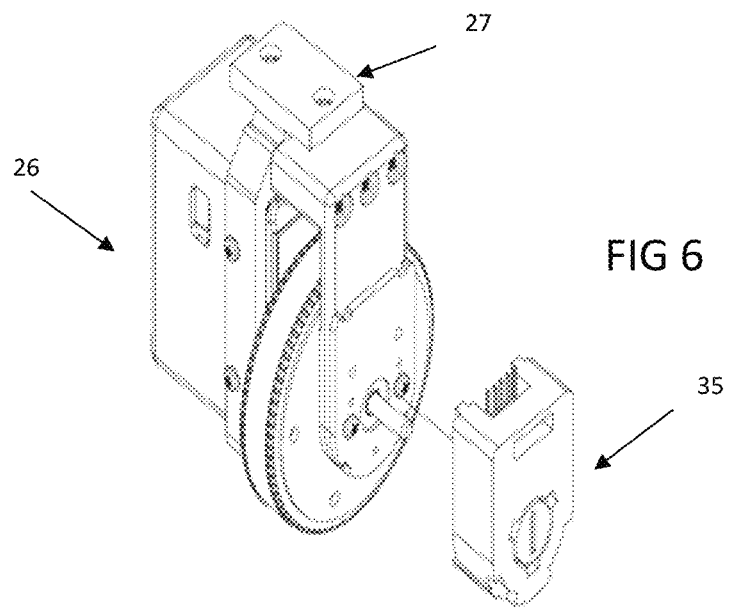
FIG. 6 shows an isometric view of the assembly of the front traction wheels with the encoder cap and with the encoder according to the invention.
Figure 7:
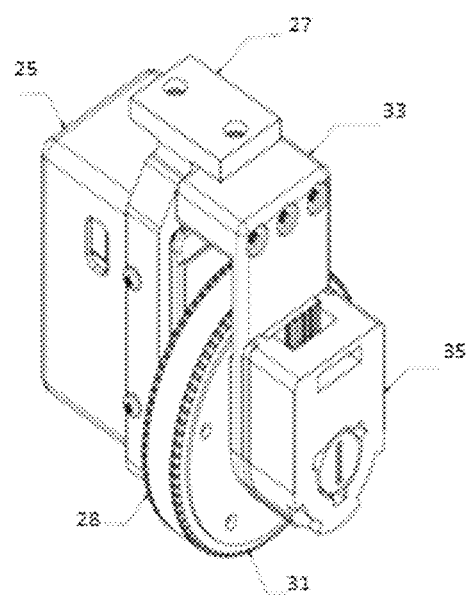
FIG. 7 shows an isometric view of the finished assembly of the front traction wheels with the servomotor coupled thereto in accordance with the invention.
Figure 8:
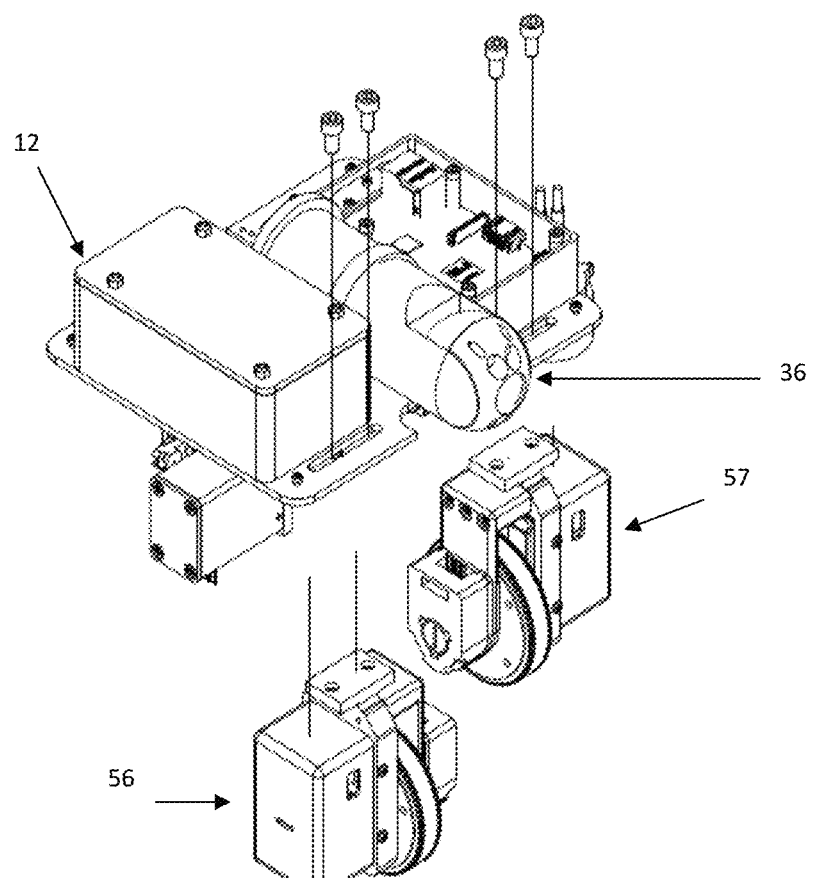
FIG. 8 shows an isometric view of the assembly of the front traction wheels with the vehicle housing according to the invention.
Figure 9:
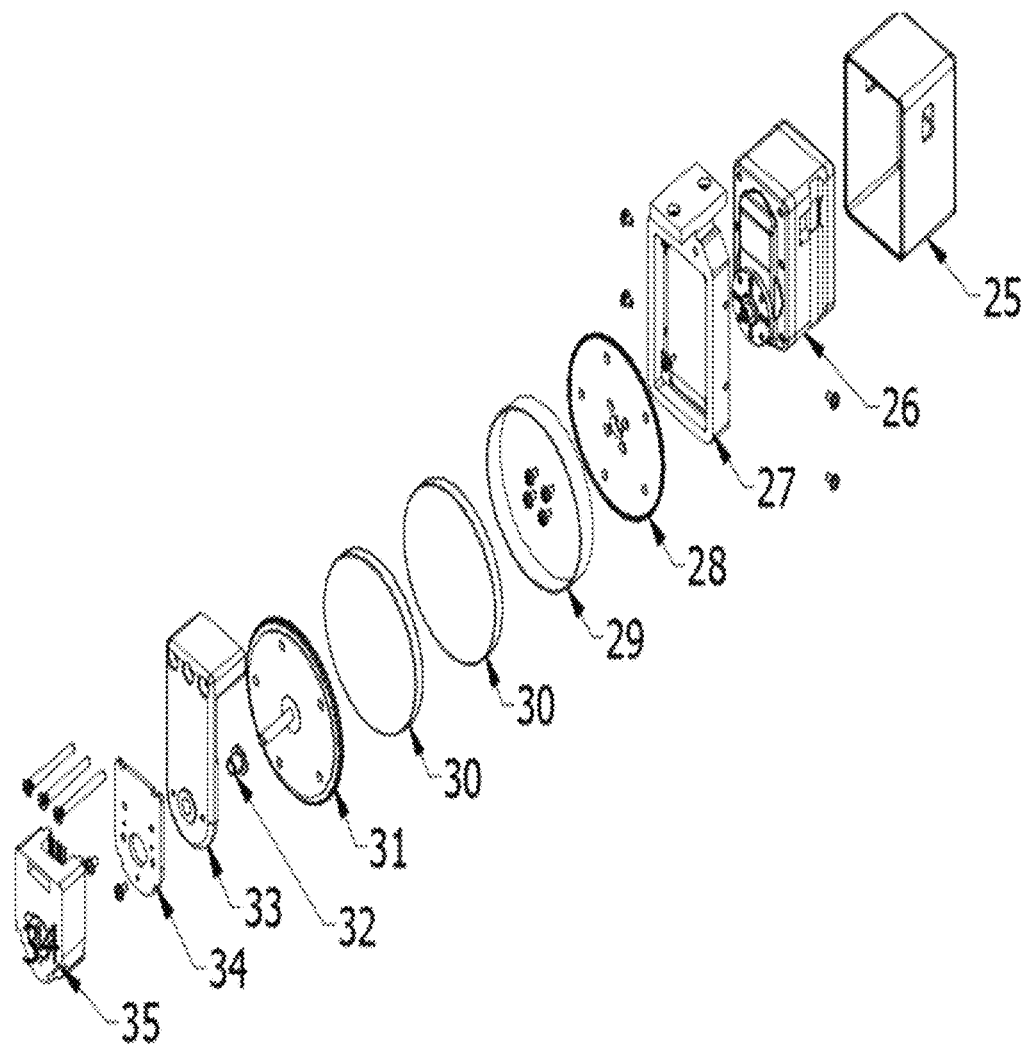
FIG. 9 shows an isometric view of the exploded view of the front traction wheels with their corresponding servomotor and encoder according to the invention.
Figure 10:
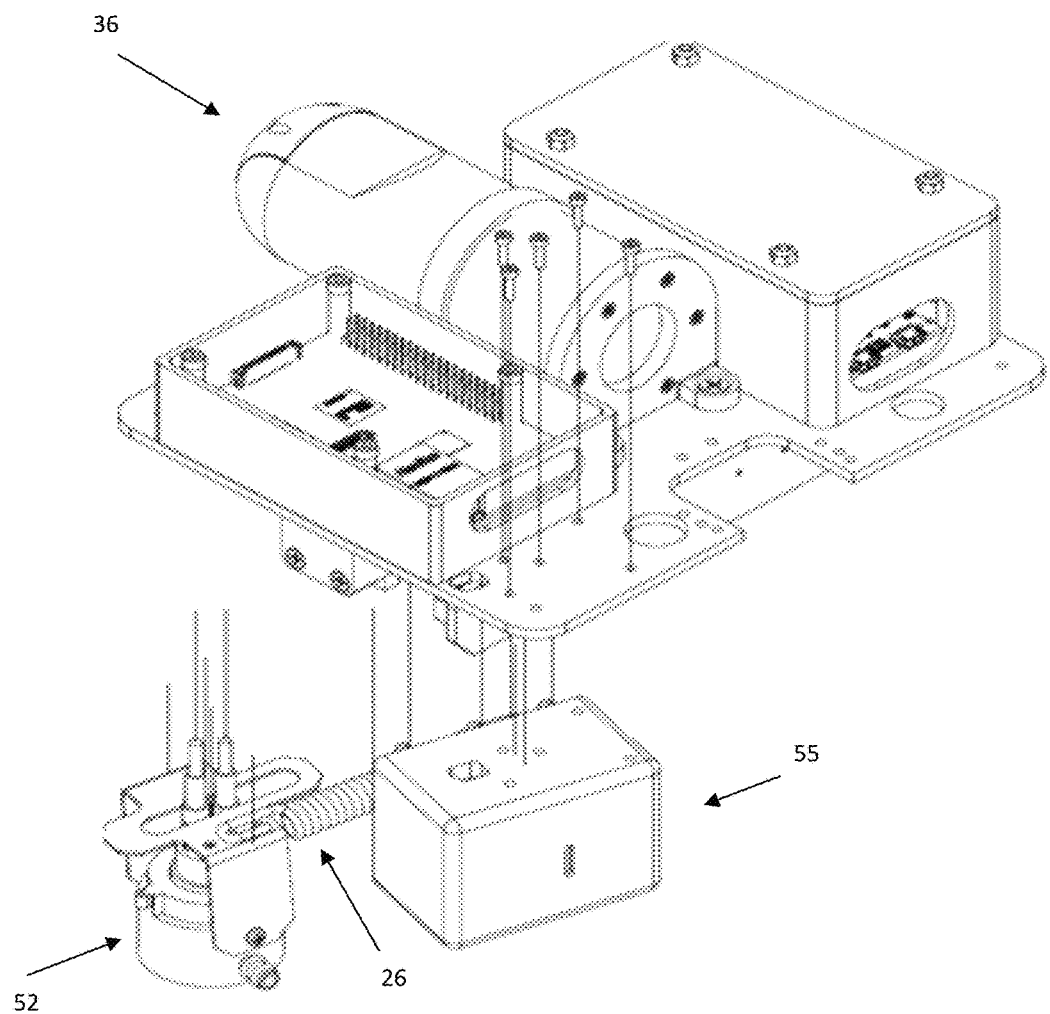
FIG. 10 illustrates an isometric view of the assembly of the ultrasonic inspection device with its corresponding servomotor engaging the vehicle housing.
Figure 11:
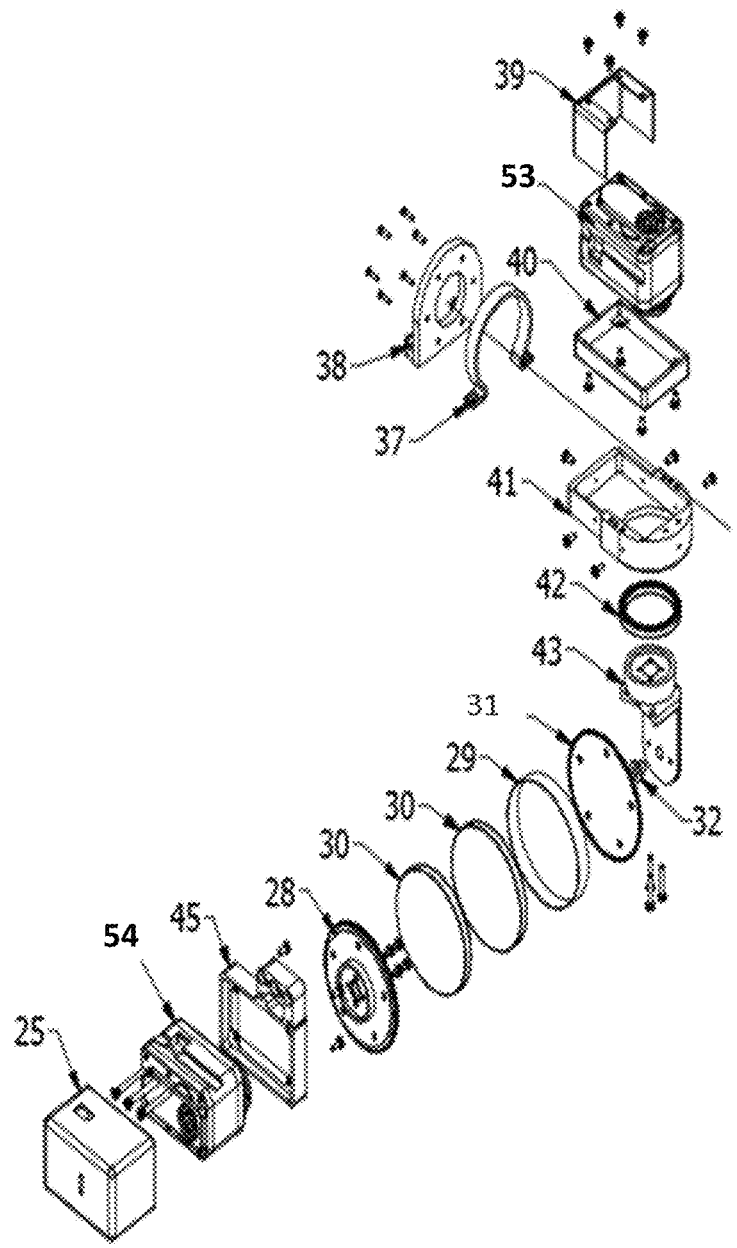
FIG. 11 shows an isometric view of the rear wheel traction assembly with the rudder servo motor and the auxiliary servo motor according to the invention.
Figure 12:
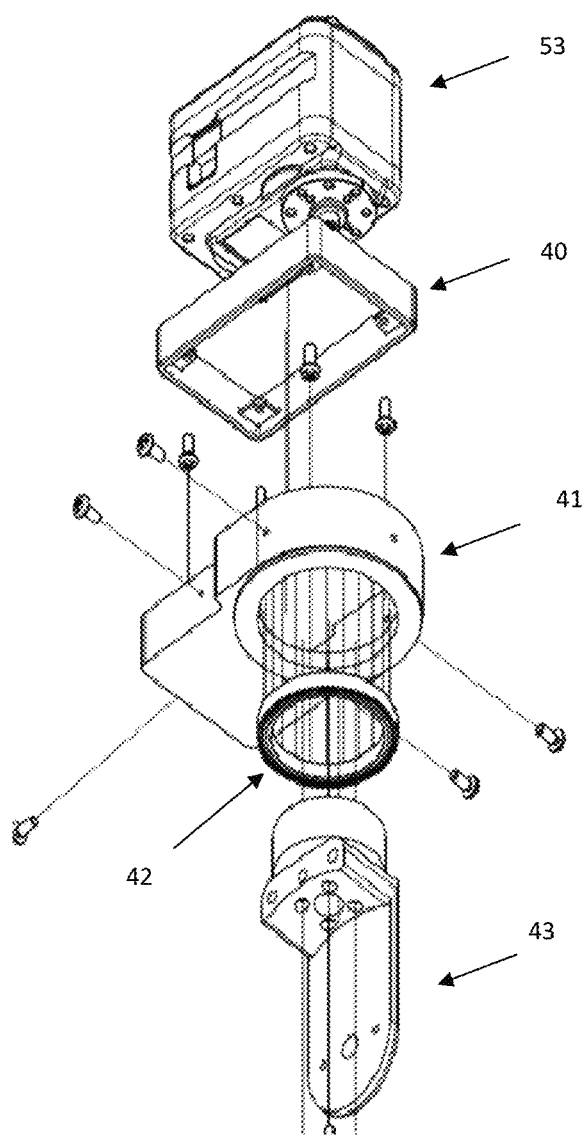
FIG. 12 illustrates an isometric view of the rear traction wheel assembly wherein the coupling of the rear wheel support with the rudder beam and the rudder servomotor according to the invention is shown.
Figure 13:
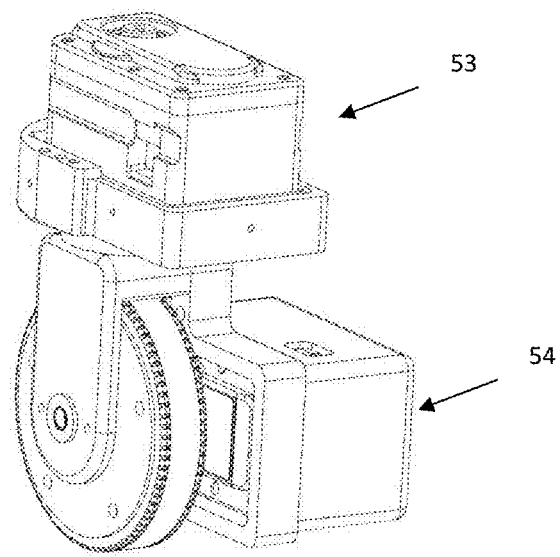
FIG. 13 shows an isometric view of the final assembly of the rear traction wheel with its two servomotors coupled according to the invention.
Figure 14:
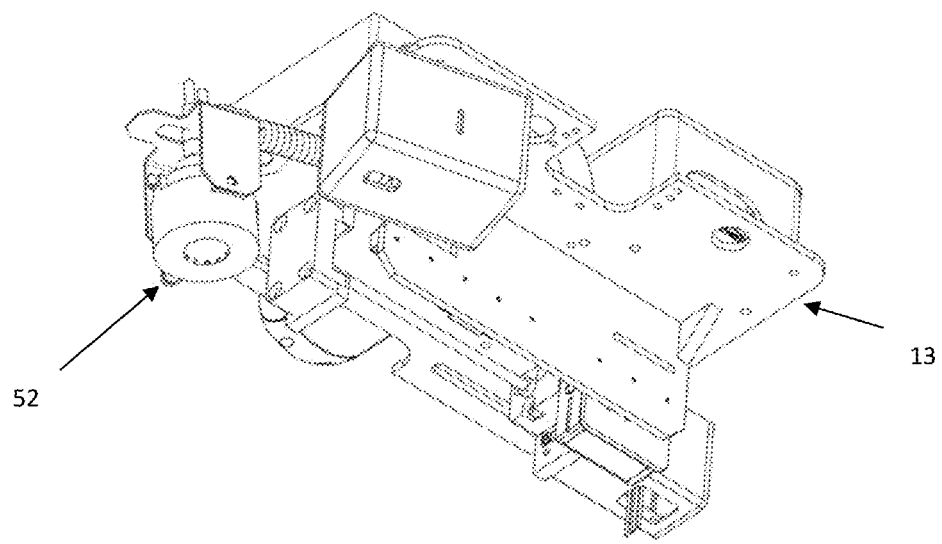
FIG. 14 illustrates a lower isometric view of the vehicle housing with its assembled parts except the front and rear traction wheels according to the invention.

Characteristic details of the invention are described in the following paragraphs, which are for the purpose of defining the invention but without limiting the scope thereof. The present invention aims at proposing a solution for automating or facilitating the inspection process or activity of pipelines or other components through a vehicle for external inspection by laser, ultrasound and visual, in a compact, light and easy to handle manner, Designed to be positioned in pipes exposed to an aggressive environment, where the paint protection layers are degraded in general or in areas that are affected by corrosion producing layers of oxide film, and that by such cause the adhesion force to be lost as well as to be out of the reach of the inspector, either by the height or position of the platform structure, variable distance up to 8 meters (26.25 ft), in different pipe diameters from 101.6 mm (4 inches) to 1066.8 mm (42 inches) and can be placed vertically, horizontally and at any point on the perimeter of the pipe on the surface of the pipe to obtain wall thickness records in carbon steel pipe, Through a single ultrasound equipment, without requiring installation of scaffolding.

Accordingly, the present invention relates to a vehicle for external inspection of pipes formed by a base (13), an upper cover (1) arranged on the base (13) forming a vehicle housing, a master card box (6) arranged inside the vehicle housing, fixed to base (13), a master card box lid (2) which closes the upper part of master card box (6), spacers (5) preferably of 6 mm (0.236 in) arranged between the master card (4) and the bottom of the master card box (6), second spacers (3) preferably of 15 mm (0.591 in) arranged between the Master card (4) and master box cover (2).

A slave card box (12) disposed inside the vehicle housing, fixed to the base (13), a slave card (10) disposed inside the slave card box (12), a slave card box lid (7), spacers (11) preferably 3 mm (0.118 in) arranged between the bottom of the slave card box (12) and the slave card (10), a connection card (9) arranged on the slave card (10) inside the slave card box (12), spacers (8) preferably 10 mm (0.394 in) arranged between the connection card (9) and the slave card box lid (7).

A linear actuator (19) which drives the worm screw coupled to a linear actuator flange (16), a linear actuator assembly (18) coupled to a linear actuator housing (20) wherein is placed the linear actuator (19), said linear actuator housing (20) is coupled at one end to a cover lid of linear actuator (21), a laser sensor (17) coupled to the sensor holder (15) coupled to the linear actuator flange (16), coupled to the linear actuator worm screw (19), a linear guide (22) parallel to the worm screw and coupled to the base (13), a linear guide carriage (23) slidably coupled to the linear guide (22) and to sensor holder (15), a second linear actuator assembly (24) fixed to the opposite side lower part of the base (13) where the end of worm screw is fixed, so that the flange (16) slides on the worm screw.

A pair of forward, left and right front drive wheels (56 and 57) preferably straights, each conformed by an intelligent servomotor (26), a servomotor housing (25) for receiving or host the intelligent servomotor (26), a support for a front wheel servomotor (27) wherein coupled the servomotor housing (25), a first servomotor wheel cover (28) coupled to the servomotor, a pair of neodymium circular discs (30), a circular cover (29) which housing the neodymium discs 30, coupled to the first wheel cover 28, a second wheel cover 31 which is on the side of an encoder 35, a front wheel support 33 coupled to the servomotor support (27), an encoder 35 externally coupled to the front wheel support (33) adjacent the second wheel cover (31), a wheel bearing 32 by which the axis of the second wheel cover 31 is coupled to the front wheel support 33, an encoder lid 34 coupled to the encoder 35.

A visual inspection chamber 36 supported by a rest or clamp camera 37, which is secured to a camera support plate 38 which in turn is fixed to the base 13.

A rear traction wheel (58) aligned longitudinally between the front wheels (56 and 57), the rear traction wheel (58) formed by a rudder servomotor support cover (39) attached to the base (13), a support of rudder servomotor (40) coupled to the support cover (39), an intelligent rudder servomotor (53) coupled to the rudder servo support (40), a rudder wheel bearing holder (41) coupled to the support (40), a rudder bearing 42, a rear wheel support (43), which has a circular head coupled to the intelligent rudder servomotor (53) and wherein also engaged the rudder bearing (42), So that the rear wheel support (43) is rotatable by controlling said rotation by the intelligent rudder servo motor (53), a first wheel cover (31) coupled by a bearing (32) to the rear wheel support (43), a circular cover (29) coupled to the first wheel cover (31) and which houses a pair of Neodymium circular discs 30, a second wheel cover 28 closing the circular cover 29, said second wheel cover 28 is coupled to a rear intelligent servo motor 54, so as to direct the translational advancement of the wheel Rear, said rear servomotor (54) is housed in a servomotor housing (25) itself which is coupled to a rear wheel servomotor support (45).

An thickness inspection system by ultrasonic conformed by a servomotor clamping box (46) coupled to the base (13), an auxiliary intelligent servomotor (55) for control of ultrasonic device housed in the housing (46), A servomotor box lid 48, an arm or spring 47 which is assembled at one of its ends to the spring articulator 49 which is assembled to an auxiliary servomotor 55, and at its opposite end to a transducer support (50) attached to the coupler (52), which carries in its central part a transducer or piezoelectric sensor (51) of the ultrasonic.

The vehicle for external inspection of pipes can be divided into the following systems:

a) Driving System

A driving system comprising three wheels, two front wheels (56 and 57) and one rear (58), two front servomotors (26), one for each front wheel, a rudder servomotor (53) for rear wheel rotation (58) and a rear servomotor 54, these servomotors 53 and 54 coupled to the rear wheel 58 and two encoders 35, one for each front wheel 56 and 57.

The front wheels (56 and 57) assembled on the front of the vehicle are formed by two steel covers: a first inner side cover (28) and a second exterior side cover (31), both covers (28 and 31) designed with a chamfer, the first cover (28) with the chamfer on the inner edge and the second cover (31) with the chamfer on the inner edge.

The rear wheel 58 assembled at the rear of the vehicle is formed by two covers: a first inner side cover 28 and a second exterior side cover 31; both of the covers designed with a chamfer, the first cover (28) with the chamfer on the inner edge and the second cover (31) on the outer side with the chamfer on the inner edge.

The chamfer of the covers (28 and 31) is in each of the toothing formed in the inner side edge of the covers, said teeth having a radius which allow the wheel to increase the contact area between the wheel and the Surface of a pipe from 10.16 cm (4 inches) in diameter.

The wheels are magnetized by a pair of circular discs neodymium (30) type cylindric with axial magnetization and poles on flat faces.

The neodymium discs are assembled between the two steel wheel covers (28 and 31), placing a magnetic pole (North and South) on each wheel cover (28 and 31). Neodymium discs are assembled without drilling to maintain their magnetic strength.

In wheel assembly, the toothing of both covers 28 and 31 are arranged so that a toothing of the inner side cover proceeds and precedes a toothing of the outer side cover.

By means of this arrangement of the toothing of each cover (28 and 31), "North-South" magnetic circuits are generated around the perimeter of the wheel, increasing its peel strength by the magnetic adhesion force generated by said circuits.

The vehicle servomotors (26, 54 and 53) are controlled from the control software (control interface) installed on the server or master card (4) and accessed by an HTML (HyperTex Markup Language) from a computer, tablet type, Laptop, etc.

The control interface provides the slave card 10 data, integer numbers decimal base type, which is interpreted and converted to PWM (pulse width modulation) by the slave card (10), these pulses are directed towards the servomotors (26, 54 and 53) to generate controlled movement of the vehicle.

B) Ultrasonic Thickness Inspection System

The ultrasonic thickness inspection or measurement system is comprised of an auxiliary servo motor (55), a spring arm (47), an coupling device of ultrasonic sensor, a hydrocoupler, a coupling fluid feed hose (Water), a mini pump for feeding the coupling fluid (water) and a thickness measuring equipment or fault detector.

The arm or spring 47 is assembled at one of its ends to the spring articulator 49 which is assembled to an auxiliary servomotor 55, and at its opposite end to a transducer support 50 attached to the coupler 52, Which carries in its central part a transducer or piezoelectric sensor (51) of the ultrasonic.

The auxiliary servo motor (55) of the thickness inspection system by ultrasonic is controlled from the control software (control interface) installed on the server or master card (4) and wirelessly accessed via HTML (HyperTex Markup Language) from a computer of the Type Tablet or Laptop.

The arms in conjunction with all of the aforementioned parts are driven by the auxiliary servomotor (55) in an upward and downward movement for placement and removal of the transducer or piezoelectric sensor (51) on the tubing surface (engage and uncouple) the sensor piezoelectric of ultrasonic.

The instrumented device of thickness measurement by ultrasonic is further integrated with an thickness measuring device by ultrasonic, a piezoelectric type transducer (51) of 1.5875 cm (⅝ diameter) of 5 Mhz, a 15 m cable, a feed system of fluid (Water) to the location of the transducer, which is formed by a system of pumping and laminar transport of the fluid driven by a 12 V DC motor.

This method of mechanical type, based on acoustic impedance, in which the ultrasonic sound wave is transmitted through electrical pulses generated by the apparatus and which are led by a coaxial cable to the transducer (51), which by means of a crystal having piezoelectric properties transforms them into mechanical vibrations and propagates them inside the pipe until it is reflected back to the transducer 51, which transforms them into electrical impulses that are analyzed and represented on a screen with an image digitizer, recording and storing in the ultrasound apparatus the wave path, reflected energy and distance traveled, information used in the evaluation of the mechanical integrity.

C) Image Inspection System

The image inspection system is composed of a pipe inspection video camera (36) which is equipped with a lighting system with six leds and two degrees of freedom in movement, these degrees of freedom allow you to rotate the camcorder 360° around its axis and rotate 280° perpendicularly with respect to its axis.

The camcorder's movements, focus of the image, intensity of illumination and recording are controlled remotely by means of a console connected to the camera by means of a cable of 15 meters in length.

The video camera (36) can focus images from a distance of 12 mm (0.474 in) up to more than 5 meters (16.4 ft).

D) External Corrosion Inspection System by Laser

The elements that make up the depth measurement system in corrosion are the following:

The laser measuring sensor is a distance sensor (17) with very small dimensions, which measures under the principle of triangulation, this sensor has a class 2 red laser emitting diode, with a wavelength of 650 nm, a beam of point type, and a sensor of CCD type that detects the light beam to perform the measurement. It has a measuring range from 16 mm to 120 mm, range corresponding to an analog output of 0 to 10 linear volts. Physically it has a rectangular shape, and it has a Zinc housing with protection IP67, against dust, humidity and temperature, it has an M8 connector (8 mm) of 4 pins; VDC (12 volts), Ground, Analog Output (0-10 volts) and Teach to calibrate. It has immunity to ambient light greater than 30000 Lux.

The distance sensor (17) will be used to measure the distance from a healthy surface to a lower point, ie the depth of the corrosion, the calibration is done with reference to a healthy surface and from that value will be measured corrosion depths on the external surface of the pipes, this sensor is of point type so it would be displaced linearly with a mechanism to form a "dotted line" and cover a length of 10 cm corresponding to the length of the actuator stroke, one of the points is taken a measurement, the sensor will provide a voltage output as a function of depth, which will be read through an analog pin of a development card responsible for processing the signal and convert it into the actual depth measurement (numerical value of depth).

The laser sensor (17) is the fundamental part of the corrosion system as it delivers a voltage relative to the depth being measured in the pipe, which is mounted on a linear actuator (19) which moves from one end to the Other (from right to left). The connection between the master card (4) and the sensor (17) is made by means of one of the analog input pins of the connection card (9) (electronic card for processing of data) and this converts it into a magnitude interpretable by the user.

The linear actuator 19 is a mechanical device consisting of a stepper motor of NEMA 8 type very small, which has a bipolar coil array fed at 7.5 Volts, of 200 steps per revolution with an external actuator integrated into the motor of worm type with a linear advance of 8 mm per revolution and a total stroke of 100 mm. It has the flange nut counterpart 16, which is attached to two linear guides 22 along the worm, this flange 16 supports a sensor holder 15 which serves to house the sensor 17 and move it linearly throughout your career. All this is supported by a thin plate that serves to align the guides (22) and the motor in addition to giving robustness to the complete linear actuator.

The linear actuator (19) has the function of moving the sensor (17) along a specific straight path or path to perform a swept or scan forming a dotted line, as a stepper motor, it can also determine the position of the sensor (17) according to the number of steps advanced by it and with the aid of a position encoder to verify the accuracy of the advance.

The linear actuator 19, being a stepper motor, is connected to an electronic connection card 9, and this connection card 9 in turn is connected to the slave card 10 (for movement control) which gives information on how the linear actuator (19) is to be moved to carry out the sensor 17 stroke, in addition to that in each displacement the control slave card (10) is capable of receiving the positioning data for processing the forward position. The encoder 35 is a device which transforms and encodes the angular position of a rotating mechanical element to electronic signal pulses coupled to the front wheels 56 and 57 of the vehicle; The encoder (35) is fed at 5V DC (direct current volts) and generates pulses processed or interpreted by the master card (4).

Depending on the displacement of the linear actuator 19, the encoder 35 generates a number of pulses which translate into distance, that is, if the linear actuator 19 advances 8 mm in one revolution and the encoder 35 generates 80 Pulses, each pulse equals a linear advance of 0.1 mm.

The rotary encoder (35) interacts with the linear actuator (19) to know the position of the laser sensor (17) and take the measurements at a certain displacement, in addition to the encoders (35) also interacting with the front wheels 56, 57 because they allow, in addition to measuring the distance traveled, to accurately move the scanner and to move the line generated by the actuator 19 and the laser 17 and convert it to a 3D surface.

The electronic cards that interact with the system are 2, the movement control card and the minicomputer:

Motion control card or slave card (10) based on an ARM microcontroller from 32 bits to 84 Mhz which has analog inputs, pulse width modulation outputs to control the motors, digital inputs and outputs, serial communication, USB connection, powered at 12 VDC, enough to supply the scheduled tasks.

It will receive instructions from the master card 4 to control the wheels' motors for forward, reverse and scan mode, and will control the linear actuator 19 to move the sensor 17 and convert the voltage signal Sent by the sensor (17) to a depth in millimeters, processing the signals from the encoders (35) and the sensor (17) will form the coordinates and this data will be transferred for storage via a serial port via USB to the Master card (4). Interaction of the slave card or movement control card (10) with the other elements of the external surface measurement system:

This card 10 interacts with all the electromechanical parts of the vehicle, and is exclusively dedicated to the control thereof and processing of the positioning data and measurements of sensor 17.

The master card (4) acts as a minicomputer with an ARM microprocessor at 700 Mhz with 40 general purpose inputs and outputs, USB ports, Ethernet connection, SD card slot for operating system storage and data powered at 5 VDC.

This master card (4) will offer the graphical environment to the operator to control the movement of the wheels of the vehicle by means of a Tablet/Laptop, through a graphical interface the operator sends with a virtual joystick the orders of movement to the motors and will be ordered to store in a removable medium all the collected information of the scans, besides graphically showing the topography of the scanned corrosion.

The master card 4 interacts with the slave card or motion control card 10 by sending commands through the serial port such as the speed of the motors or the start of the scan. Wirelessly via WiFi will show the operator a graphical environment in the browser of a portable device with Web browser with the movement and scan controls, in addition to the results obtained in 3D graphics.

The connector card (9) or integrating of electrical and electronic components is interconnected with the slave card (10), master card (4), power source (not shown), encoders, servo motors, linear actuator, proximity sensor and laser sensor, Includes control drivers, voltage converters and heat sink.

The master card (4) is a minicomputer in charge of receiving the position and distance data from the slave card for processing and displaying them to the operator, as well as sending movement instructions or movement commands to the slave card (10), the master card (4) hosts the graphical user interface (dashboard) and is visible on Tablet/Laptop of wirelessly accessed.

The slave card (10) responds to commands released from the control interface by executing servomotors motion control processes, for forward, backward, right and left vehicle movement, communicates with the master card (4) via USB cable to send the position information obtained by two encoders (35), assembled on the two front wheels, and to receive the movement commands of the master card (4).

The slave card (10) and master card (4) communicate with each other via a USB cable (inside the vehicle), while the master card (4) communicates wirelessly by WiFi with a router/modem to the Tablet or processor (at floor level).

The master card (4) processes data and presents it to the user.

The slave card (10) stores measurements and sends to the master card (4) when the scanning is completed.

The tablet asks the master card (4) to display the graphical user interface.

A modem allows all devices to connect wirelessly.

The laser sensor (17) is a device that measures distance by triangulation in a single point, to obtain a topography of the stains of corrosion will be made a meshing of points from samples taken from the surface of the pipe, these points are used for the reconstruction of the surface in precise coordinates in addition to the exact depth measurement.

To achieve this, 3 coordinates are required;

X: Is the distance at which the linear actuator moves the sensor in a sweep.

Y: It is the distance that the same vehicle moves forward after each sweep.

Z: It is the measurement of the surface itself, ie the depth from a reference or healthy surface.

Graphing these 3 coordinates will give a 3D representation of a corrosion spot including the depth of each point and the total length of the stain.

The vehicle will measure the third axis ("Y" axis); The corrosion depth ("Z" axis) shall be measured using the laser sensor (17), the corrosion length ("X" axis) shall be obtained by means of the linear actuator (19) and the third plane of the measurement shall be obtained by moving the vehicle wheels on the surface of the pipe, by measuring this displacement with an encoder 35 on each wheel, the actuator 19 and the laser sensor 17 generate a line on the axis "X" And "Z" (B-Scan) scrolling on the "Y" axis of the plane as the vehicle wheels advance until a C-Scan type graph is generated.

With this C-Scan type graph, a corrosion topography is obtained on the surface of the externally inspected pipe.

Functioning

The operation of the vehicle is divided into 3 functions to be executed within a main cycle within the control microprocessor or slave card (10).

Movement function

Vehicle status

Measurement of external surface corrosion

When the vehicle is switched on, the first task is to initialize the variables, communications and dynamic parts in a HOME position, ie wheel servomotors 26, 53 and 54, linear actuator 19 of the measuring device and auxiliar servomotor 55 for the transducer of ultrasonic, in order to prepare the vehicle for use in pipelines and to prevent the transducer 51 from being damaged by an inappropriate position of the spring or arm 47.

Once initialized and ready for operation, the controller card or slave card 10 will wait for the instructions from the master card 4 in a defined format, a character is sent from the master card 4 to the slave card or controller 10, then the slave or controller card 10 responds with another character that the master card 4 interprets as a stable connection. The main function is the movement function, this function will always be running until another action is ordered, this to move the vehicle over the pipes.

The motion function interprets numerical values representing the direction of rotation, power and speed of the servomotors 26, 53 and 54 of the wheels as well as the position of the arm 47 of ultrasonic.

The master card 4 defines these numbers which are integer values coming from the movement control (crosshead) of the interface software, and sends them through the communication port between the two cards.

The interface software is installed on the master card 4 and is operated from tablet of rugged use.

The slave or controller card 10 receives this data and processes them, in addition to performing calculations to realize a turning radius in the 3-wheel system, the two fixed front 56 and 57 and the movable rear 58 through a servomotor 53 that transmits rotational movements, the resulting information is sent to the servo motors through serial communication, as these are intelligent digital servomotors and controlled by means of commands.

As long as the servomotors are instructed to move, a subroutine will read the pulses of the encoder 35 of the wheels, count these pulses, and store those pulses which are variables that will refer to the slave card 10 to determine the distance traveled by the vehicle.

The traction system of the vehicle consists of 3 wheels as a tricycle, the rear wheel 58 has freedom of steering;

Consists of 2 front wheels 56 and 57 and 1 rear wheel 58, 2 intelligent servomotors 26 and 54 provide movement to the front wheels, forward and backward, in addition to a third servomotor 53 installed in the rear wheel to provide translational and turning movements to this.

The best coupling configuration for this design is 3 points, because there is a minimum gap between wheels that is required to accommodate the measuring devices and encoders. This restriction of space does not allow the use of 4 points in a 4-inch tube, because at the moment of turning, one of the four points of support would not come into contact with the pipe and would cause its detachment.

The front wheels are parallel, assembled in vertical potion allowing them to adhere to the pipe in the longitudinal position and perpendicular to the pipe, as well as facilitating passage over a ½ inch diameter clamp without detaching from the pipe.

The wheel is made of two covers and a ring covering 2 neodymium discs, the covers have concave radios on their circumference, making it possible for the vehicle to jump on clamps, making a coupling of these concave radios of the wheel on the circumference of the clamp and to be able to jump it avoiding that the wheel slips and skids when trying to pass it.

The positioning of the wheels and their attachment to the body of the vehicle or frame or housing have defined a turning and steering path in all three wheels. Turns and changes of direction are provided through the rear wheel 58 instrumented with the rudder servo motor 53, which obeys the movements through the program located on the slave or controller card 10, allowing the operator to give the turn command from the software interface, located on a Tablet of rough use. The front wheels 56 and 57 of the vehicle are driven by the movement and direction of the rear wheel.

The status function of the vehicle is responsible for providing information to the operator about the current state of the vehicle such as the distance traveled and the remaining battery level:

It reads the battery voltage at that time and stores it in a variable to determine the remaining battery level.

It is sends to call the stored distance data and the now processed data of battery level.

Both are sent to the master card 4 and are shown to the operator in the interface located in the tablet of rough use.

The last function is the external surface corrosion measurement function, it is the most robust part of the programming since it includes closed loop control, measuring sensor voltage readings and reading encoder pulses 35 to high speed for the tripping the Readings of the laser 17, including the precise movements of linear actuator 19 and wheels. When the master card 4 executes the scanning action, the motion function is stopped while the scanning is active, this to prevent that the operator from interfering with the automatic scanning movements and producing a wrong reading, the motion function is re-enabled when the scan is finished, either because the scanning area ends or because the user finishes it before scanning the area.

When the vehicle to be connected, it is initialized and the linear actuator 19 is set to HOME or "0", the scanning is performed from left to right or from top to bottom making a mesh of points.

At the start of the scan, the sensor 19 takes a measurement which corresponds to the coordinate 0,0, Z where the first number indicates the advance of the linear actuator on the "X" axis, the second number is the advance of the own vehicle with the wheels on the "Y" axis, and "Z" is the depth measurement, this data is stored in an external memory SD.

The linear actuator 19 starts its stroke in 100 mm "X" advancing and returning with a programmed subroutine which contains a specific acceleration and velocity that allows the laser sensor 17 mounted on the actuator 19 to be moved at a speed of 6 cm/s in a distance of 100 mm, this movement ends until the 100 mm of advance in the direction of the "Y" axis is reached.

While the actuator 19 is moving, an encoder adapted to the stepper motor of the actuator will be generating electrical pulses according to the movement, the pulses are as a function of the distance that the actuator moves so that when counting a certain number of pulses we will know the exact position of the sensor in the actuator, this will allow us to notify the slave or control card 10 when and at what position of the linear actuator 19, take the measurement of the sensor 17 in the "X" axis and record these data required for graphical generation of results (meshing).

When the sensor 17 arrives at the end of the race, a 2D sweep has been carried out because the "X" coordinate will reach 100 mm and the "Y" coordinate will still be "0". At that time the linear actuator 19 stops its movement, and the slave or controller card 10 will move the servomotors 26 and 54 of the wheels so as to have an advance of equal magnitude between each sweep 2D. This is achieved thanks to the encoders 35 of the wheels, which allow to measure the angular displacement and convert it to a forward distance, this distance will be the "Y" coordinate.

The coordinate "X" is the advance of the sensor 17 through the linear actuator 19 making a 2D sweep, the coordinate in "Y" is the advance of the vehicle itself on the pipe and the coordinate "Z" is the measuring of the depth of corrosion at each point.

Once the scan is completed, the option to continue with another 10×10 cm scan is displayed on the interface from where the vehicle was positioned and a scan of 10×20 cm or save the current scan and continue to inspect another area.

During scanning all coordinates and measurements are stored in the slave card or controller 10, upon completion of the scan, these data are sent to the master card 4 which processes them to display a surface graph to the operator indicating the length of the corrosion and the maximum depth. Once all data is sent, they are deleted from the slave or controller card 10, since they are stored in a temporary memory space in the slave or controller card 10, it is not possible to perform information backups only on the master card 4.

It should finally be understood that the vehicle for external inspection of pipes according to the invention are not limited to the modality or modalities described above and that experts in the field would be enabled by the teachings herein established to effect changes in the composition of the Inspection vehicle of the present invention, the scope of which will be established exclusively by the following claims.

The invention claimed is:

1. A vehicle for external inspection of pipes comprising: a base, an upper cover arranged on the base forming a vehicle housing; a master card; a slave card connected to the master card; a pair of preferably straight, left and right magnetic traction wheels; a pair of intelligent servomotors each coupled to its corresponding front traction wheel; a servomotor housing for receiving or housing the intelligent servomotor; a servomotor support of front wheel, wherein the servomotor housing is engaged; an encoder on each front traction wheel, each being externally coupled to a front wheel support; a wheel bearing by means of which the front wheel drive shaft is coupled to the front wheel support; a rear traction wheel longitudinally aligned between the front wheels, the rear traction wheel formed by a rudder servo motor support cover fixed to the base, a support of rudder servo motor coupled to the rudder wheel bearing holder, an intelligent rudder servomotor coupled to the support of rudder servomotor, a rudder wheel bearing holder coupled to the base piece, a rudder bearing, a rear wheel support, which has a circular head coupled to the intelligent rudder servo motor and wherein the rudder bearing is also engaged, so that the rear wheel support is rotatable by controlling said rotation by the intelligent rudder servomotor, said rear traction wheel is coupled to a rear intelligent servo motor, so as to direct the translational advancement of the rear wheel, said rear servo motor is housed in a servo motor housing which is coupled to a rear wheel servo motor support; a laser sensor coupled to a slidable linear actuator to inspect the external corrosion of the pipes.

2. A vehicle for external inspection of pipes according to claim 1, characterized in that the front traction wheels are formed by a first servomotor wheel cover coupled to the intelligent servomotor, a pair of neodymium circular discs, a circular cover housing the neodymium disc, coupled to the first wheel cover, a second wheel cover which is on the side of the encoder.

3. A vehicle for external inspection of pipes according to claim 1, characterized in that the rear wheel is formed by a first wheel cover coupled by a bearing to the rear wheel support, a circular cover coupled to the first wheel cover and which houses a pair of neodymium circular discs, a second wheel cover closing the circular cover.

4. A vehicle for external inspection of pipes according to claim 1, further comprising: a linear actuator having a worm screw along which a linear actuator flange is displaced, a linear actuator assembly coupled to a linear actuator housing wherein the linear actuator is housed, said linear actuator housing is coupled at one end to a cover lid of linear actuator, a laser sensor coupled to the sensor holder coupled to the linear actuator flange coupled to the linear actuator worm screw, a linear guide parallel to the worm screw and coupled to the base, a linear guide carriage slidably coupled to the linear guide and the sensor holder, a second linear actuator assembly fixed to the opposite side lower part of the base where the end of the worm screw is fixed, so that the flange slides on the worm screw.

5. A vehicle for external inspection of pipes according to claim 1, further comprising: a visual inspection chamber supported by a camera rest which is fixed to a camera support plate which in turn is fixed to the base.

6. A vehicle for external inspection of pipes according to claim 1, further comprising: an thickness inspection system by ultrasonic, which is formed a servomotor clamping box coupled to the base, an auxiliary intelligent servomotor of ultrasonic device control, housed in clamping box; an servomotor box lid, an arm or spring is mounted at one of its ends to the spring articulator which is assembled to an auxiliary servomotor, and at its opposite end to a support transducer attached to the coupler, which carries in its central portion a transducer or piezoelectric sensor of the ultrasonic.

7. A vehicle for external inspection of pipes according to claim 1, characterized in that the front and rear traction wheels servomotors are controlled remotely by means of control software (control interface) installed on the server or master card.

8. A vehicle for external inspection of pipes according to claim 6, characterized in that the auxiliary servo motor is remotely controlled by means of control software (control interface) installed on the server or master card.

9. A vehicle for external inspection of pipes according to claim 1, further comprising a master card box arranged inside the vehicle housing, fixed to the base, arranged inside the master card box, a master card box lid which closes the top of the master card box.

10. A vehicle for external inspection of pipes according to claim 9, further comprising spacers of 6 mm arranged between the master card and the bottom of the master card box, a second spacers of 15 mm arranged between the master card and the master card box lid.

11. A vehicle for external inspection of pipes according to claim 1, further comprising a slave card box arranged inside the vehicle housing, fixed to the base, where the slave card is housed, a slave card box lid.

12. A vehicle for external inspection of pipes according to claim 11, further comprising spacers of 3 mm (0.118 in), disposed between the bottom of the slave card box and the slave card, a connection card arranged on the slave card inside the slave card box, spacers 10 mm (0.394 in) arranged between the connection card and the slave card box lid.

13. A vehicle for external inspection of pipes according to claim 1, characterized in that the front traction wheels have encoder lid coupled to the encoder.

14. A vehicle for external inspection of pipes according to claim 1, characterized in that the master card is a minicomputer in charge of receiving the position and distance data from the slave card for processing and displaying them to the operator, as well as sending instructions of movement or movement commands to the slave card, the master card hosts the graphical user interface (control board) and which is visible on a wirelessly accessed tablet/laptop.

15. A vehicle for external inspection of pipes according to claim 1, characterized in that the slave card responds to commands released from the control interface by executing servomotor movement control processes, for the movement of the vehicle forward, backward, right and left, communicates with the master card via universal serial bus (USB) cable, to send position information obtained by two encoders, assembled on the two front wheels, and receive the movement commands of the master card.

16. A vehicle for external inspection of pipes according to claim 1, further comprising a connector card or integrating electrical and electronic components is interconnected with the slave card, master card, power source, encoders, servomotors, linear actuator, laser sensor, including control drivers, voltage converters and heat sink.

\* \* \* \* \*